ORNAMENTAL AND FRUITING PEACH TREE
Filed Nov. 20, 1950 2 SHEETS—SHEET 1
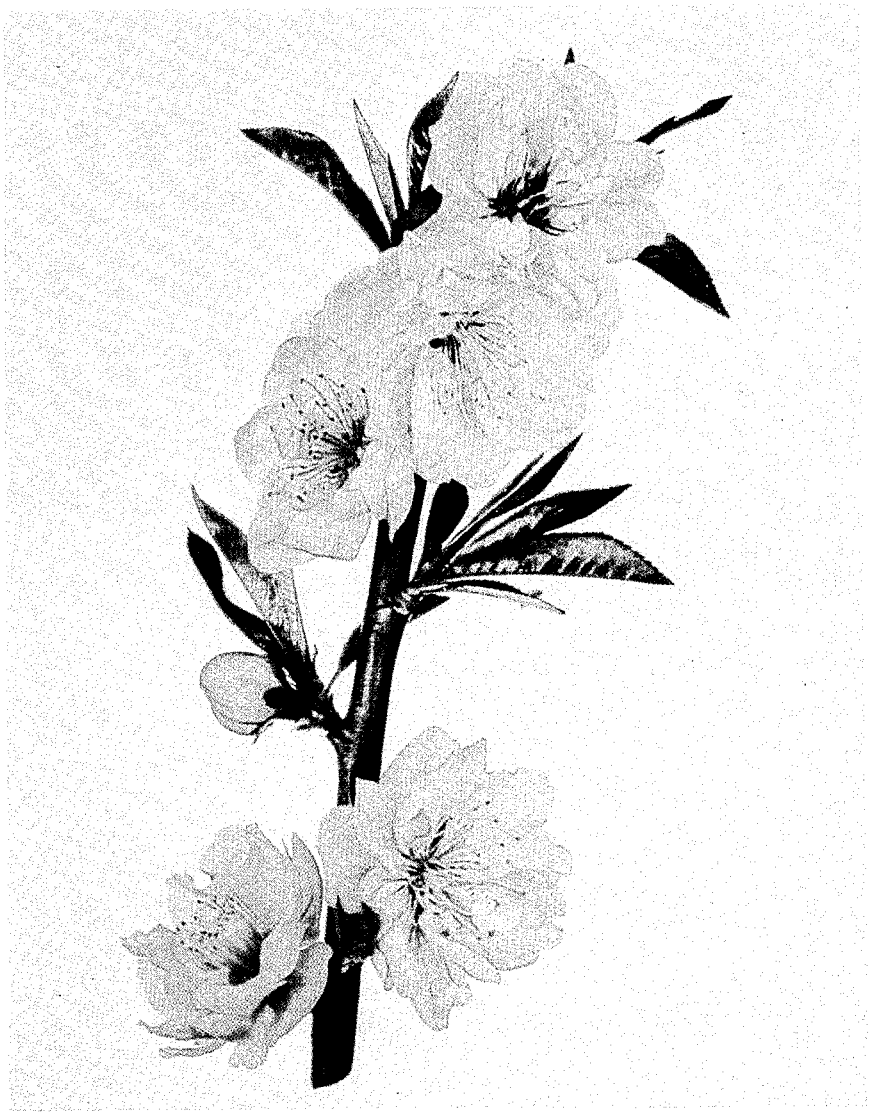
Inventor.
W. E. Lammerts
By: Robb & Robb
Attorneys.

ORNAMENTAL AND FRUITING PEACH TREE
Filed Nov. 20, 1950 2 SHEETS—SHEET 2
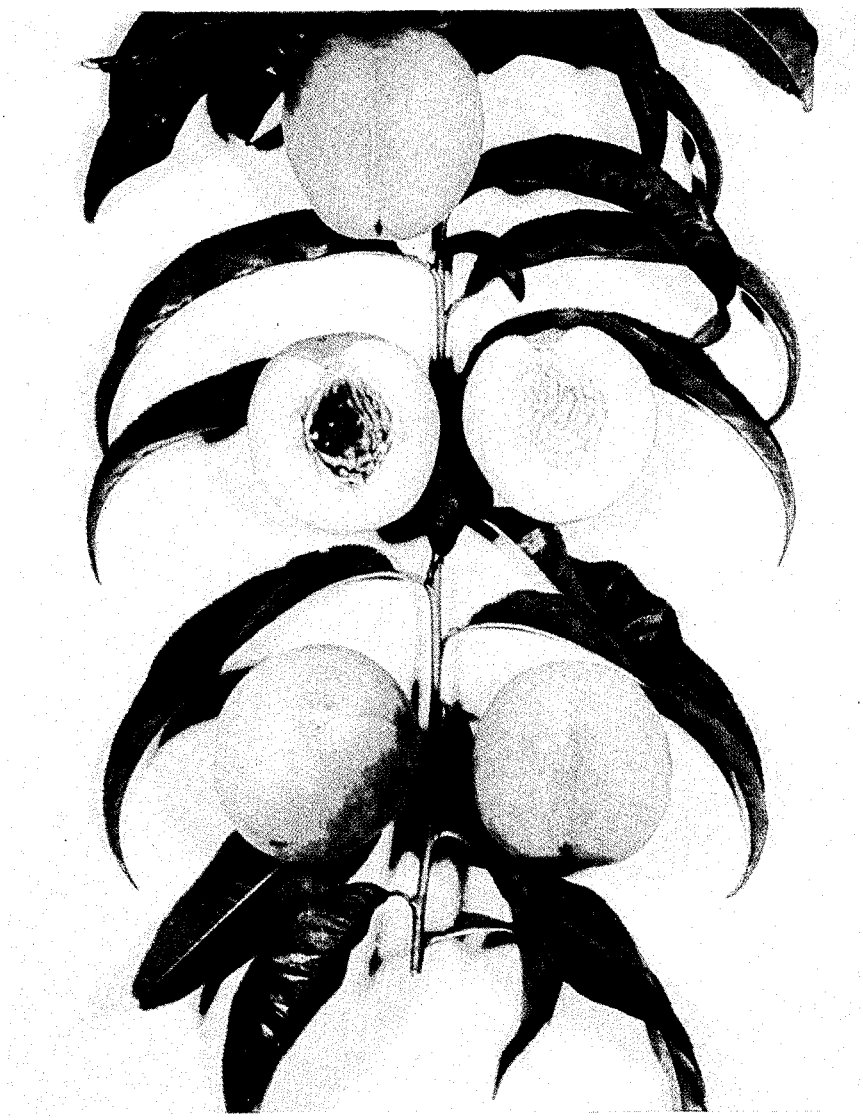
Inventor.
W. E. Lammerts
By: Robert Cobb
Attorneys.

Patented May 6, 1952

Plant Pat. 1,092

UNITED STATES PATENT OFFICE 1,092

ORNAMENTAL AND FRUITING PEACH TREE

Walter E. Lammerts, La Canada, Calif., assignor to Descanso Distributors, Inc., La Canada, Calif., a corporation of California Application November 20, 1950, Serial No. 196,636

1 Claim. (Cl. 47—62)

The present invention relates to a new and distinct variety of ornamental and fruiting peach tree, originated as a self-pollinated seedling of a double-flowering, unnamed and unpatented seedling obtained from growing seed from open-pollinated fruit of "Chinese Dwarf Evergreen" (unpatented) × "Rio Oso Gem" (Plant Patent No. 84).

In points of novelty and distinctiveness, the above-noted breeding has produced a peach tree having a unique combination of characteristics unlike any known variety of which I am aware, and making this variety outstanding from all others.

The chief distinguishing characteristic of this new variety resides in its abundant production of large, double flowers having from sixteen to nineteen large and predominately dark pink or light red petals, thereby making it a very attractive ornamental flowering peach.

In addition to the aforementioned ornamental characteristic, the new variety is importantly characterized by its production of very highly colored, freestone, yellow-fleshed fruit of medium size, resembling somewhat the late "Crawford" (unpatented) in general size and appearance. The juice, however, is much more abundant and rich in flavor, while the fruit has a firm and superior crisp texture.

A still further important and advantageous characteristic of the new variety is its short chilling requirement, which makes it particularly well adapted to warm winter climates where it is useful as a home-use tree by combining attractive ornamental flowering qualities with good production of fruit of exceptionally fine edible qualities, in contrast to the general rule that the fruit of most flowering peaches heretofore known is small, usually clingstone, unattractive in appearance, bitter and inedible.

Asexual reproduction of this new variety by budding near McFarland, California, shows that the foregoing characteristics come true to form and are established and transmitted through succeeding propagations.

The accompanying drawings show specimens of the flowers, fruit and foliage of the new variety, the fruit being shown in both elevation and in plan, as well as in section both with and without the stone.

The following is a detailed description of the new variety, based upon observations of specimens grown at La Canada, California, with color terminology in accordance with British Royal Horticultural Color Standards, except where general color terms of ordinary dictionary significance are obvious:

Dates first and last picking: August 16–20.

Tree: Large; vigorous; upright; open; vase formed; productive; regular bearer.

*Trunk.*—Medium stocky; medium smooth.

*Branches.*—Medium stocky; medium smooth; color near light garnet brown Plate 00918/3 above and near Scheeles green green Plate 860/2 lower surface; glossy. Lenticels—numerous.

*Leaves.*—Length—3¾ inches to 4¾ inches. Width—1 inch to 1¾ inches. Medium size; acuminate to lanceolate; medium thick; near Parsley green Plate 00962; smooth. Margin—finely serrate. Petiole—medium length; medium thick. Glands—average number—2 (rarely 3 or 4). Opposite; medium size; reniform; green; position immediately below leaf blade at upper part of petiole. Stipules—practically absent.

Flowers: Flower Buds—large; long; obtuse; plump; free; slightly pubescent.

*Flowers.*—Dates first and full bloom—January 30th; full bloom February 16th. Early compared with other varieties. A distinguishing features of this new peach variety is the large number of large flowers, 1¾ inches in diameter having 16 to 19 large petals making a very showy ornamental appearance in the early spring. Color—Rose Pink, Plate 427/3, at margin of petals grading to Camellia Rose, Plate 622/2, then shading to Phlox Pink, Plate 625/2, grading into Phlox Pink, Plate 625/1, toward base of petal, and actual base of petal Spirea Red, Plate 025/1.

Fruit: Maturity when described—eating ripe. Date—August 16th.

*Size.*—Uniform; medium. Diameter axial—2 to 2¼ inches. Transverse in suture plane—2 to 2¼ inches. At right angles to suture plane—2⅛ to 2½ inches.

*Form.*—Uniform; usually symmetrical to slightly unsymmetrical; globose to broadly ovoid.

*Suture.*—Distinct; extends from base to about one-half inch beyond apex; has slight depression beyond pistil point.

*Ventral surface.*—Strongly lipped toward base throughout both sides. Lips—equal to slightly unequal.

*Cavity.*—Rounded; elongated in suture plane with suture showing on one side. Depth—¼ inch. Breadth—½ inch.

*Base.*—Rounded.

*Apex.*—Rounded. Pistil point—apical.

*Stem.*—Length—¼ inch; medium stout; glabrous. Adherence to stone—medium strong.

*Skin.*—Medium thick; medium tender; tenacious to flesh. Tendency to crack—none in dry season. Color—Chrysanthemum Crimson, Plate 824, to Garnet Brown, Plate 00918/3 at base with patches or stripe (where shaded by branch) of Primrose Yellow, Plate 601/1, diffusing into peppering or dotting of Blood Red, Plate 820, and this grading into Chartreuse Green, Plate 663/1, on both cheeks and toward apex. Down—moderate; short; rolls up when rubbed.

*Flesh.*—Color—yellow with red next to stone. Surface of pit cavity—red with yellow fibres. Amygagalin—scant. Juice—abundant; rich. Texture—firm; fine; crisp. Fibres—few; fine; tender. Ripens—even. Aroma — pronounced. Eating quality—good.

*Stone.*—Free; sometimes retains short fibre-like threads along ridges. Size—medium; length 1⅛ to 1¼ inches; breadth ⅞ to 1 inch; thickness ¾ to ⅞ inch. Form—ovoid; pointed. Base—oblique. Hilum—narrow; oblong. Apex—acute. Sides—unequal; curved on right and left sides. Surface—irregularly furrowed throughout; pitted throughout. Ridges—jagged toward base. Pits—circular and elongated.

Ventral edge—thin with wing toward base. Dorsal edge—narrow with narrow grooves toward base. Color of stone—near Erythrite Red, Plate 0027. Tendency to split—slight in dry season.

Use: Local; dessert.

Keeping quality: Medium.

Resistance to: Disease—good resistance to *Exoascus deformans* (peach leaf curl), as determined by observation and comparison with standard peach varieties grown under comparable conditions and which ordinarily require spraying each spring under conditions prevailing at La Canada, California, whereas my new variety has not required spraying. Insects—good resistance to red spider, as determined by observation and comparison with standard varieties grown under comparable conditions at La Canada, California.

Shipping quality: Medium.

I claim:

A new and distinct variety of ornamental and fruiting peach tree, characterized as to novelty by its abundant production of large, many-petalled, highly ornamental double flowers of predominantly dark pink color, by its production of highly colored, yellow-fleshed, edible, free-stone, juicy fruit, rich in flavor and of firm and crisp texture, and by its short chilling requirement suitable to warm winter climates, substantially as shown and described.

WALTER E. LAMMERTS.

No references cited.